US005616558A

United States Patent [19]

Ohneda et al.

[11] Patent Number: 5,616,558
[45] Date of Patent: Apr. 1, 1997

[54] MEDICAMENTS COMPRISING GLICENTIN AS ACTIVE INGREDIENT

[75] Inventors: Akira Ohneda, Sendai; Kazuyuki Sasaki, Tokyo; Yohei Natori, Tokyo; Tomohisa Nagasaki, Tokyo, all of Japan

[73] Assignee: Nisshin Flour Milling Co., Ltd., Tokyo, Japan

[21] Appl. No.: 83,501

[22] Filed: Jun. 30, 1993

[30] Foreign Application Priority Data

Jul. 13, 1992 [JP] Japan ................................. 4-185066

[51] Int. Cl.$^6$ ..................... A61K 38/00; A61K 38/26; C07K 14/00; C07K 14/605
[52] U.S. Cl. ........................................... 514/12; 530/324
[58] Field of Search ............................ 530/324; 514/12

[56] References Cited

FOREIGN PATENT DOCUMENTS

WO90/11296  10/1990  WIPO .

OTHER PUBLICATIONS

Thieden et al., Biochemica & Biophysica Aeta, 675, 163–70 (1981).
Holst, J., Gastro Nérologer, 84, 1602–13, (1983).
Marco et al., J. Clin. Endocr. 33, 318 (1971).
Ahren, B. and I. Lundquist, Horm. Net. Res. 12, 582–586 (1986).
Ohneda et al, Chemical Abstracts, vol. 105, No. 17, 27 Oct. 1986, Columbus, Ohio, Abstract No. 146676, "Effect of Glicentin–Related Peptides on Glucagon Secretion in Anesthetized Dogs", p. 115.
Holst et al, Febs Letters, vol. 211, No. 2, Jan. 1987, Amsterdam NL, "Truncated Glucagon–Lik e Peptide I, an Insulin–Releasing Hormone from the Distal Gut", pp. 169–174.
Ahren et al, Chemical Abstracts, vol. 94, No. 7, 16 Feb. 1981, COlumbu, Ohio, Abstract No. 416 70c, "Effects of Glicentine on Insulin Secretion", p. 69.
A. Ohneda, et al., Tohoku Journal of Experimental Medicine, vol. 129, 1979, pp. 207–217.

A. Ohneda, et al., Diabetes, vol. 24, No. 9, 1975, pp. 811–819. "Glucagon Response to Arginine after Treatment of Diabetes Mellitus".
C. Morgan, et al., Diabetes, vol. 12, No. 2, 1963, pp. 115–126. "Immunoassay of Insulin: Two Antibody System".
A. Ohneda, et al., Horm. Metab. Res., vol. 9, 1977, pp. 447–452. "Effect of Intrapancreatic Administration of Vasocative Intestinal Peptide upon the release of Insulin and Glucagon in Dogs".
G. Bell, et al., Nature, vol. 304, Jul. 1983, pp. 368–371. "Exon duplication and divergence in the human preproglucagon gene".
A. Ohneda, et al., Horm. Metab. Res., vol. 8, 1976, pp. 170–174. "Purification of Canine Gut Glucagon–Like Immunoreactivity (GLI) and Its Insulin Releasing Activity".
D. D'Alessio, et al., Diabetes, vol. 38, Dec. 1989, pp. 1534–1538. "Effects of Glucagonlike Peptide I–(7–36) on Release of Insulin, Glucagon, and Somatostatin by Rat Pancreatic Islet Cell Monolayer Cultures".
T. Matsuyama, et al., Diabetes Research and Clinical Practice, vol. 5, 1988, pp. 281–284. "Glucagon–like peptide–1 (7–36 amide): a potent glucagonostatic and insulinotropic hormone".
R. Ebert, et al., Diabetes/Metabolism Reviews, vol. 3, No. 1, 1987, pp. 1–26. "Gastrointestinal Peptides and Insulin Secretion".
S. Seino, et al, FEBS, vol. 203, No. 1, Jul. 1986, pp. 25–30. "Mutations in the guinea pig preproglucagon gene are restricted to a specific portion of the prohormone sequence".
L. Thim, et al., Regulatory Peptides, 2 (1981), pp. 139–150. "The Primary Structure of Porcine Glicentin (Proglucagon)".
V. Mutt, et al, Advances in Metabolic Disorders, vol. 11, 1988, pp. 141–162. "Gastrointestinal Hormones".

*Primary Examiner*—Howard E. Schain
*Assistant Examiner*—P. Lynn Touzeau
*Attorney, Agent, or Firm*—Oblon, Spivak, McClelland, Maier & Neustadt, P.C.

[57] ABSTRACT

Agents for stimulating insulin secretion and for treating diabetes which comprise glicentin as an active ingredient.

4 Claims, 1 Drawing Sheet

5,616,558

MEDICAMENTS COMPRISING GLICENTIN AS ACTIVE INGREDIENT

FIELD OF THE INVENTION

This invention relates to agents for stimulating insulin secretion and therapeutic agents for diabetes, which comprise glicentin as an active ingredient and also the invention relates to the use of glicentin as therapeutic agents for diabetes by administration of glicentin to stimulate insulin secretion, thus increasing the blood level of insulin.

BACKGROUND OF THE INVENTION

Glicentin is a peptide comprising 69 amino acid residues, regardless of origin, as a major component of gut glucagon-like immunoreactants which are also called gut glucagon-like immunoreactivities (gut GLIs). The peptide contains the entire sequence of glucagon in positions 33–61 which is extended at the amino terminus via Lys-Arg with the 1–30 sequence, glucagon-related pancreatic peptide (or glicentin-related pancreatic peptide) and at the carboxy terminus via Lys-Arg with a hexapeptide (positions 64–69) (Volume 11 Gastrointestinal Hormones edited by V. Mutt, Noboru Yanaihara and Chizuko Yanaihara, pp. 141–162, Academic Press, Inc. 1988).

L. Thim & A. J. Moody have established the primary structure of porcine glicentin (Regulatory Peptides, 2 (1981), 139–150). S. Seino et al have suggested the amino acid sequences of human, bovine, hamster, rat and guinea pig glicentin from their preproglucagon sequences (FEBS, Vol. 203, No. 1, pp. 25–29, 1986). Glicentin and glucagon are produced by tissue specific processing from the same precursor, preproglucagon. Glucagon is formed in pancreas and glicentin in intestine. It is known that glucagon counteracts the blood glucose-lowering action of insulin by stimulating glyconeogenesis and glycogenolysis (R. Ebert et al., Diabetes Metabolism Review, Vol. 3, No. 1, 1–26 (1987)). Glucagon-like peptide-1 (GLP-1) (1–37) produced by tissue specific processing from the same preproglucagon is a 37-amino acid polypeptide hormone and the peptide derived from it, GLP-1 (7–36 amide) is a 30 amino acid polypeptide hormone. Those hormones are known to have an insulin releasing function (T. Matsuyama et al., Diabetes Res. and Clinical Practice, Vol. 5, 281–284 (1988), D. A. D'Alessio et al., Diabetes, Vol. 38, 1534–1538 (1989)).

Some investigators reported that a fraction of Peak II (rich in glucagon of low molecular weight) prepared by fractionation of glucagon-like immunoreactivity (GLI) extracted from the mucosa of small intestine in dogs exhibited the stimulation of insulin secretion, whereas a fraction of Peak I (rich in glicentin) did not exhibit it (A. Ohneda et al., Horm. Metab. Res. Vol. 8, 170–174 (1976)).

On the other hand, the biological action of glicentin has not been confirmed. It is unknown on what tissue or cell glicentin acts directly. Glicentin so far isolated and purified is an origin of other mammalian animals than humans. Human glicentin has not been isolated as a purified product because of the difficulty in an availability of the materials for extraction, i.e., human gut. Thus, the physiological roles of human glicentin have not been elucidated.

The present inventors were successful in synthesizing DNA corresponding to the amino acid sequence of human glicentin which was deduced by Graeme I. Bell et al. (Nature, Vol. 304, 368–371 (1983)) from the sequence of human preproglucagon gene, preparing a recombinant DNA vector using the synthesized DNA and then producing human glicentin from a host cell transformed by the recombinant DNA (Japanese Patent Kokai Hei 4-364199). This success leaded to easy availability of human glicentin in a large amount and as a purified product.

With a rise in the standard of living, the number of diabetic patients is yearly increasing. The prevalence for the past 30 years shows a rapid increase tendency as much as 30 times or more. The morbid state of diabetes will be caused by an absolute or relative lack of an insulin function which plays a central part in the regulation of blood glucose. The main method for the treatment of diabetes includes an alimentary therapy and an administration of insulin.

Sulfonylurea is known as a drug for stimulating insulin secretion. However, this drug has the disadvantages in that over- or continuous-administration leads to a risk of causing hypoglycemia and enough attention is required to keep a normal blood glucose level. For the patients suffering from hepatopathy and nephropathy, a special care is further required in the administration, since the drug or its metabolite is accumulated. In addition, an administration of the drug to gravida is not recommended because of its placental passage and an administration to a nursing woman is impossible because of its easy migration to milk. Therefore, there is a desire to develop an insulin secretomotory agent having high safety and less side effects.

SUMMARY OF THE INVENTION

In view of the above situations, the present inventors have made a continuing study on agents for stimulating insulin secretion and found that human glicentin possesses a strong insulin releasing activity, thus leading to the present invention.

The present invention provides an agent for stimulating insulin secretion which comprises glicentin as an active ingredient. The glicentin used in the invention can stimulate a secretion of insulin from pancreas with no rise in blood glucose and therefore can be used for the treatment and prophylaxis of diabetes. Thus the present invention further provides a therapeutic agent for diabetes which comprises glicentin as an active ingredient.

DETAILED DESCRIPTION OF THE INVENTION

Figure 1:
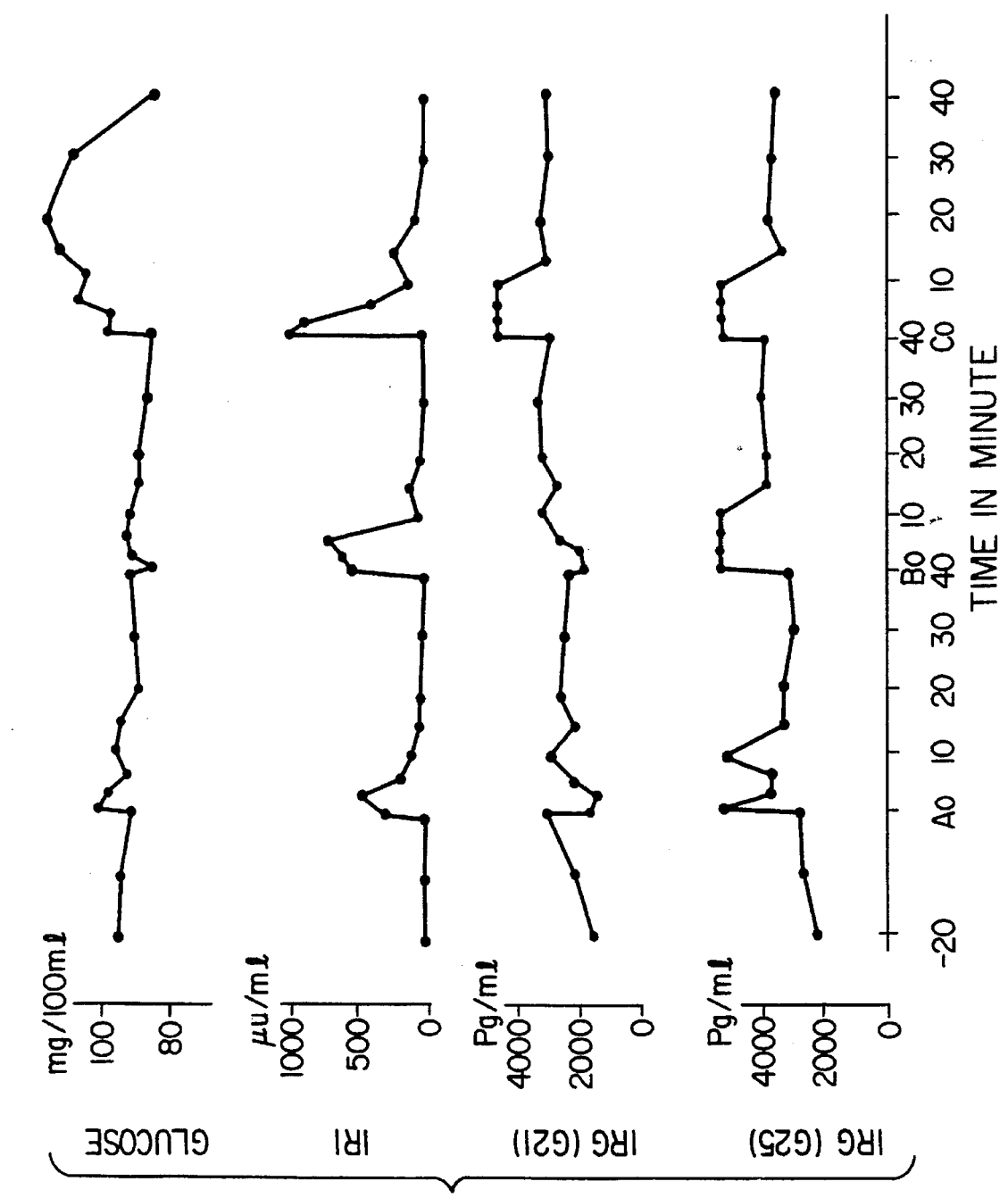
FIG. 1 represents temporal variations in the levels of blood glucose level (BGL), insulin (IRI), glucagon (IRG(G21)) and glucagon-like immunoreactivity (IRG(G25)) during the administration of glicentin and glucagon in a test animal.

In the present invention, an administration of glicentin brings about the stimulation of insulin secretion which leads to the treatment and prophylaxis of diabetes caused by the physical condition of insufficient insulin secretion.

Glicentin which can be used in the present invention includes any glicentin of an animal origin such as human, porcine, bovine, hamster, rat and guinea pig, as well as glicentin containing methionine (Met) added to the N-terminus, which are prepared by a genetic engineering procedure or a synthetic process. Preferably, human glicentin is used in view of an undesirable allergic reaction or the like produced when being administered to humans. More preferably, there is used human glicentin (natural type) not containing methionine (Met) added to the N-terminus.

Human glicentin (natural type) has the following amino acid sequence (SEQ. ID NO:1):

---

Arg—Ser—Leu—Gln—Asp—Thr—Glu—Glu—Lys—Ser—Arg—Ser—Phe—Ser—Ala—Ser—Gln—
Ala—Asp—Pro—Leu—Ser—Asp—Pro—Asp—Gln—Met—Asn—Glu—Asp—Lys—Arg—His—Ser—
Gln—Gly—Thr—Phe—Thr—Ser—Asp—Tyr—Ser—Lys—Tyr—Leu—Asp—Ser—Arg—Arg—Ala—
Gln—Asp—Phe—Val—Gln—Trp—Leu—Met—Asn—Thr—Lys—Arg—Asn—Arg—Asn—Asn—Ile—
Ala

---

Further, human glicentin containing methionine (Met) added to the N-terminus has the following amino acid sequence (SEQ ID NO:2):

---

Met—Arg—Ser—Leu—Gln—Arg—Thr—Gln—Glu—Lys—Ser—Arg—Ser—Phe—Ser—Ala—Ser—
Gln—Ala—Asp—Pro—Leu—Ser—Asp—Pro—Asp—Gln—Met—Asn—Glu—Asp—Lys—Arg—His—
Ser—Gln—Gly—Thr—Phe—Thr—Ser—Asp—Tyr—Ser—Lys—Tyr—Leu—Asp—Ser—Arg—Arg—
Ala—Gln—Asp—Phe—Val—Gln—Trp—Leu—Met—Asn—Thr—Lys—Arg—Asn—Arg—Asn—Asn—
Ile—Ala

---

The above human glicentin can be prepared by a genetic engineering procedure or a synthetic process from a gene of the DNA sequence corresponding to the above amino acid sequence. An example of the genetic engineering procedure is a process of producing a desired human glicentin which comprises preparing a synthetic gene encoding human glicentin amino acid sequence of the following DNA sequence (SEQ ID NO:3) which has been suggested by the present inventors in Japanese Patent Kokai Hei 4-364199, introducing the synthetic gene into plasmid, transforming *E. coli* with the resultant plasmid and culturing the transformant.

---

5' CGTTCC CTGCAGGACA CTGAAGAAAA ATCTCGTTCT TTCTCTGCTT CTCAGGCTGA
3' GCAAGG GACGTCCTGT GACTTCTTTT TAGAGCAAGA AAGAGACGAA GAGTCCGACT
CCCACTGTCG GATCCAGACC AGATGAACGA AGACAAACGT CATTCTCAGG GTACTTTCAC
GGGTGACAGC CTAGGTCTGG TCTACTTGCT TCTGTTTGCA GTAAGAGTCC CATGAAAGTG
TTCTGACTAC TCTAAATACC TGGACTCTCG TCGAGCTGAT GACTTCGTTC AGTGGCTGAT
AAGACTGATG AGATTTATGG ACCTGAGAGC AGCTCGAGTC CTGAAGCAAG TCACCGACTA
GAACACTAAA CGTAACCGTA ACAACATCGC C 3'
CTTGTGATTT GCATTGGCAT TGTTGTAGCG G 5'

---

Other processes of producing the human glicentin include introducing into plasmid a gene of another DNA sequence corresponding to the above amino acid sequence of glicentin, transforming *E. coli, Bacillus subtilis,* yeast or other microorganism with the resultant plasmid and culturing the transformant or alternatively culturing a human glicentin productive cell. However, it should be understood that human glicentin used in the invention is not limited to one produced by the specific process and any human glicentin can be employed in the invention so far as it has the above amino acid sequence.

Usually, glicentin as the active ingredient can be administered orally or parenterally in the form of suitable pharmaceutical preparations. Such pharmaceutical preparations can be formulated in a conventional manner using one or more pharmaceutically acceptable vehicles, adjuvants and additives, e.g., binders, diluents, solubilizers, stabilizers, buffers, lubricants, coating agents, antioxidants, sweeteners, flavors, colorants and the like. Suitable preparations include powders, granules, tablets, capsules, injections, syrups, suspensions, emulsions or the like. If necessary, the active ingredient may be administered in combination with other drugs such as sulfonylurea, biguanide or the like. It may be in bilayered or multilayered tablet with other drugs. The tablets may also be coated with a conventional coating to form, e.g., sugar-coated, enteric-coated or film-coated tablets.

In the formulation of solid preparations such as tablets and capsules, there may be used suitable additives such as lactose, refined sugar, crystalline cellulose, corn starch, calcium phosphate, sorbitol, carboxymethylcellulose, gum arabic, polyvinylpyrrolidone, hydroxypropylcellulose, glycerin, polyethylene glycol, stearic acid, magnesium stearate and talc. In the formulation of liquid preparations such as injections and syrups, suitable additives may be used such as sodium chloride, sorbitol, glycerin, olive oil, propylene glycol and ethyl alcohol.

For a preferred unit dosage form for oral administration, for instance, the aqueous or oily solutions, suspensions or emulsions may contain glicentin in an amount of 0.01 to 10 rag, advantageously 0.1 to 1 mg per 5 ml and the tablets, capsules or granules may contain glicentin in an amount of 0.01 to 10 mg, advantageously 0.1 to 1 mg.

From the chemical structure, glicentin is considered to undergo a denaturation by an acid within intestine, a decomposition by digestion and a reduction in activity by such denaturation, when administered orally to human body. Therefore, it is recommendable to release the active ingredient, glicentin within intestine using an enteric coating. Thus the active ingredient is preferably coated with a conventional enteric coating agent in the oral administration. The enteric coating agents include synthetic polymers such as EUDRAGI®, polyacrylate base (available from Rohm Pharma), semisynthetic polymers such as cellulose acetate phthalate or the like.

A preferable administration of glicentin is parenteral for the reason of its not undergoing denaturation or decomposition. The parenteral administration includes subcataneous, intravenous, intramuscular and intraperitoneal injections.

Glicentin can be formulated into the aqueous or oily solutions, suspensions or emulsions. Preferably, glicentin is administered in the form of depot preparations for a prolonged effect of glicentin over a long period of time.

A dose of the active ingredient can be varied depending on the route of administration, the symptoms, age, sex and weight of patients and other factors, but suitably can be in the range so as to provide a level of 100 pM to 10,000 pM in blood. Usual parenteral dosage for adult human ranges from 0.5 µg/kg to 500 µg/kg. However, lower or higher amount may be administered within the safety range.

When 10 mg/kg of human glicentin (natural type) is intraperitoneally administered to male MALB/c mice (6 weeks age), no change in appearance is observed.

The invention is further illustrated by the pharmacological test described in the following example. Methods and Materials:

Healthy mongrel dogs weighing 13 to 17 kg were subjected to the test after an overnight fast (A. Ohneda et al., Hotre. Metab. Res., 9, 447–452 (1977)).

The animals were anesthetized with sodium pentobarbital (Nembutal®) and their abdomens were opened. A cannula for administering test solutions was inserted into the superior pancreaticoduodenal artery. A cannula for collecting blood for use in the determination of hormone was inserted into the superior pancreaticoduodenal vein. After the operation was completed, saline solution containing 0.5% arginine was infused into the pancreatic artery at a constant rate of 2 ml/min through the cannula using an infusion pump. Twenty minutes after the start of infusion, 100 pmol or 400 pmol glicentin solution containing 0.2% bovine albumin in saline solution, and then 400 ml glucagon solution containing 0.2% bovine albumin in saline solution were successively infused into the pancreatic artery for 10 minutes at an interval of 40 min. 4 ml portions of blood samples for hormone assay were collected at various intervals into a glass tube containing 1000 KIU aprotinine and 10 mg EDTA.

Measurements:

The plasma insulin was measured in accordance with a known method mentioned in C. R. Morgan et al., Diabetes, Vol. 12, No. 2, 115–126 (1963).

The plasma glucagon was measured using an antiserum (G 21) specific for the C-terminal portion of glucagon in accordance with the Ohneda et al method mentioned in A. Ohneda et al., Diabetes, Vol. 24, No. 9, 311–819 (1975).

The plasma glicentin was determined as the total glucagon-like immunoreactivity using an antiserum (G 25) which cross-reacts with the glucagon related substances in accordance with the Ohneda et al method mentioned in A. Ohneda et al., Tohoku J. Exp. Med., 129, 207–217 (1979).

The blood glucose was measured for blood drawn from the femoral artery by the glucose oxidase method using a test kit for the determination of blood glucose (available from Wako Pure Chemical Industries, Japan under the trade name of "Glucose B-Test Wako").

Results:

The results are shown in FIG. 1, in which there are demonstrated the effects of glicentin and glucagon on blood glucose, plasma insulin and plasma glucagon in the arginine loaded dogs. In FIG. 1, the abscissa axis indicates time in minutes and the infusion of arginine was started from −20 min. Ao shows the time at which glicentin begins to infuse. The glicentin solution was infused for 10 minutes from Ao min. and 40 minutes later, at Bo min., the glicentin solution was infused again for 10 minutes and 40 minutes later, at Co min., the glucagon solution was infused in the above manner. In FIG. 1, the ordinate axis indicates blood glucose (GLUCOSE), insulin level (IRI), glucagon level IRG(G 21)) and glucagon-like immunoreactivity (IRG(G 25)).

The test results reveal that the administration of glicentin stimulates insulin secretion with no change in blood glucose levels. From the fact that the glucagon level is not increased by the administration of glicentin, it is found that glicentin undergoes metabolism not to convert immediately to glucagon. Further, it is found that glicentin possesses a unique effect, insulin release stimulating effect which is distinct from that of glucagon induced from a rise in insulin level observed by the administration of glucagon.

The following examples-illustrate the formulation of typical pharmaceutical preparations.

Preparation 1 (Tablets)

0.5 g of glicentin, 2 kg of lactose, 20 g of magnesium stearate and 100 g of corn starch were mixed, the mixture was compressed, the compressed mixture was pulverized to granules. The granules were formed in a tabletting machine to tablets each containing 5.0 µg of glicentin. The tablets were coated with cellulose acetate phthalate to form enteric-coated tablets.

Preparation 2 (Syrups)

0.1 g of glicentin, 30 g of refined sugar, 26 g of 70% D-sorbitol, 0.03 g of ethyl p-oxybenzoate and 0.015 g of propyl p-oxybenzoate were dissolved in 60 g of hot water. After cooling, 0.15 g of glycerin and a solution of the flavor in ethanol were added. Distilled water was added to the mixture to make up a total amount of 100 ml.

Preparation 3 (Injections)

1 g of glicentin and 99 g of lactose were mixed and the mixture was dissolved in 1 liter of distilled water for injection. The solution was filtered through a sterile filter (e.g., a 0.22 µm membrane filter), 1 ml portions of the filtered solution were dispensed into vial bottles under sterile condition and freeze dried to provide the preparations for injection. The preparations are dissolved in distilled water on use.

Preparation 4 (Capsules)

0.5 g of glicentin, 4 kg of lactose, 1.5 kg of crystalline cellulose, 1.5 kg of calcium stearate and 3 kg of talc were mixed thoroughly, the mixture was compressed, the compressed mixture was pulverized to granules. The granules were encapsuled into two-piece capsules each containing 10.0 µg of glicentin.

---

What is claimed is:

1. A method for stimulating insulin secretion comprising: administering an effective amount of glicentin and a pharmaceutically acceptable carrier or excipient to an individual in need thereof.

2. The method of claim 1, wherein glicentin is human glicentin.

3. The method of claim 2, wherein human glicentin has the following amino acid sequence:

---

Arg—Ser—Leu—Gln—Asp—Thr—Glu—Glu—Lys—Ser—Arg—Ser—Phe—Ser—Ala—
Ser—Gln—Ala—Asp—Pro—Leu—Ser—Asp—Pro—Asp—Gln—Met—Asn—Glu—Asp—
Lys—Arg—His—Ser—Gln—Gly—Thr—Phe—Thr—Ser—Asp—Tyr—Ser—Lys—Tyr—
Leu—Asp—Ser—Arg—Arg—Ala—Gln—Asp—Phe—Val—Gln—Trp—Leu—Met—Asn—
Thr—Lys—Arg—Asn—Arg—Asn—Asn—Ile—Ala.

---

4. The method of claim 2, wherein human glicentin has the following amino acid sequence:

---

Met—Arg—Ser—Leu—Gln—Arg—Thr—Gln—Glu—Lys—Ser—Arg—Ser—Phe—Ser—
Ala—Ser—Gln—Ala—Asp—Pro—Leu—Ser—Asp—Pro—Asp—Gln—Met—Asn—Glu—
Asp—Lys—Arg—His—Ser—Gln—Gly—Thr—Phe—Thr—Ser—Asp—Tyr—Ser—Lys—
Tyr—Leu—Asp—Ser—Arg—Arg—Ala—Gln—Asp—Phe—Val—Gln—Trp—Leu—Met—
Asn—Thr—Lys—Arg—Asn—Arg—Asn—Asn—Ile—Ala

---

* * * * *

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:

(A) LENGTH: 69 amino acids
(B) TYPE: amino acid
(D) TOPOLOGY: linear (ii) MOLECULE TYPE: protein (vi) ORIGINAL SOURCE:
(A) ORGANISM: Homo sapiens (xi) SEQUENCE DESCRIPTION: SEQ ID NO:1:

| Arg | Ser | Leu | Gln | Asp | Thr | Glu | Glu | Lys | Ser | Arg | Ser | Phe | Ser | Ala | Ser |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Gln | Ala | Asp | Pro | Leu | Ser | Asp | Pro | Asp | Gln | Met | Asn | Glu | Asp | Lys | Arg |
|     |     |     | 20  |     |     |     | 25  |     |     |     |     | 30  |     |     |     |
| His | Ser | Gln | Gly | Thr | Phe | Thr | Ser | Asp | Tyr | Ser | Lys | Tyr | Leu | Asp | Ser |
|     |     | 35  |     |     |     | 40  |     |     |     |     | 45  |     |     |     |     |
| Arg | Arg | Ala | Gln | Asp | Phe | Val | Gln | Trp | Leu | Met | Asn | Thr | Lys | Arg | Asn |
|     | 50  |     |     |     | 55  |     |     |     |     | 60  |     |     |     |     |     |
| Arg | Asn | Asn | Ile | Ala |
| 65  |     |     |     |     |

(2) INFORMATION FOR SEQ ID NO:2:

(i) SEQUENCE CHARACTERISTICS:
(A) LENGTH: 70 amino acids
(B) TYPE: amino acid
(D) TOPOLOGY: linear (ii) MOLECULE TYPE: protein (vi) ORIGINAL SOURCE:
(A) ORGANISM: Homo sapiens (xi) SEQUENCE DESCRIPTION: SEQ ID NO:2:

| Met | Arg | Ser | Leu | Gln | Asp | Thr | Glu | Glu | Lys | Ser | Arg | Ser | Phe | Ser | Ala |
|-----|-----|-----|-----|-----|-----|-----|-----|-----|-----|-----|-----|-----|-----|-----|-----|
| 1   |     |     |     | 5   |     |     |     |     | 10  |     |     |     |     | 15  |     |
| Ser | Gln | Ala | Asp | Pro | Leu | Ser | Asp | Pro | Asp | Gln | Met | Asn | Glu | Asp | Lys |
|     |     |     | 20  |     |     |     | 25  |     |     |     |     | 30  |     |     |     |
| Arg | His | Ser | Gln | Gly | Thr | Phe | Thr | Ser | Asp | Tyr | Ser | Lys | Tyr | Leu | Asp |
|     |     | 35  |     |     |     | 40  |     |     |     |     | 45  |     |     |     |     |
| Ser | Arg | Arg | Ala | Gln | Asp | Phe | Val | Gln | Trp | Leu | Met | Asn | Thr | Lys | Arg |
|     | 50  |     |     |     | 55  |     |     |     |     | 60  |     |     |     |     |     |
| Asn | Arg | Asn | Asn | Ile | Ala |
| 65  |     |     |     |     | 70  |

(2) INFORMATION FOR SEQ ID NO:3:

(i) SEQUENCE CHARACTERISTICS:
(A) LENGTH: 207 base pairs
(B) TYPE: nucleic acid
(C) STRANDEDNESS: double
(D) TOPOLOGY: linear (ii) MOLECULE TYPE: Other nucleic acid;
(A) DESCRIPTION: DNA (synthetic)

(xi) SEQUENCE DESCRIPTION: SEQ ID NO:3:

```
CGTTCCCTGC AGGACACTGA AGAAAAATCT CGTTCTTTCT CTGCTTCTCA GGCTGACCCA        60
CTGTCGGATC CAGACCAGAT GAACGAAGAC AAACGTCATT CTCAGGGTAC TTTCACTTCT       120
GACTACTCTA AATACCTGGA CTCTCGTCGA GCTCAGGACT TCGTTCAGTG GCTGATGAAC       180
ACTAAACGTA ACCGTAACAA CATCGCC                                           207
```